United States Patent [19]

Hussain

[11] Patent Number: 5,710,354

[45] Date of Patent: Jan. 20, 1998

[54] PREPARATION OF BROMINATED INDANES

[75] Inventor: Saadat Hussain, Baton Rouge, La.

[73] Assignee: Albemarle Corporation, Richmond, Va.

[21] Appl. No.: 705,493

[22] Filed: Aug. 29, 1996

[51] Int. Cl.$^6$ .............................. C07C 25/22; C07K 5/03
[52] U.S. Cl. ............................................ 570/206; 524/469
[58] Field of Search ............................. 570/206; 524/469

[56] References Cited

FOREIGN PATENT DOCUMENTS 0 571 036  11/1993  European Pat. Off. ........ C07C 25/22

*Primary Examiner*—Frederick Krass
*Attorney, Agent, or Firm*—E. E. Spielman, Jr.

[57] ABSTRACT

A two step bromination process for manufacturing a polybrominated indane product such as octabromophenyl indane comprises the steps of:

(a) forming an intermediate by reacting an indane compound with bromine, under reaction conditions so as to dissolve and partially ar-brominate the indane compound to contain an average of at least about two ar-bromine atoms per molecule, and (b) catalytically ar-brominating the intermediate to obtain a polybrominated indane product, the catalytic ar-bromination occurring in the presence of an aluminum or iron containing bromination catalyst or other bromination catalyst having a catalytic activity substantially equivalent thereto and in a mole ratio of bromine to said intermediate of at least 5.

11 Claims, No Drawings

PREPARATION OF BROMINATED INDANES

This invention relates generally to the bromination of aromatic ring compounds to prepare products which are useful as flame retardants in plastics. More particularly, the invention relates to an improved process for the manufacture of brominated indanes such as phenyl indanes.

Polybrominated phenyl indanes and fire retardant polymeric compositions containing such compounds are described in European Patent Application No. 571,036. The polybrominated phenyl indanes are prepared by mixing a phenyl indane, such as 1,3,3-trimethyl-1-phenyl indane, and bromine in a solvent using a metal or metal halide Lewis acid catalyst such as iron or aluminum chloride. During this process, undesirable impurities are produced due to cleavage of the 5-membered ring at the benzylic carbon. Also, the product contains 10 percent or more of partially brominated materials ($Br_{5-6}$ isomers). This reduces yields and can introduce color bodies into the product.

A process for the bromination of diphenylalkanes which is described in PCT Application Publication No. WO 96/15087, pre-mixes the diphenylalkane and bromine such as in an in-line mixer or mixing nozzle and quickly feeds the mixture, preferably within about 2 seconds of its formation, into additional bromine containing a catalyst. This process works well for brominating the diphenylalkanes.

An improved process has now been found which produces polybrominated indanes in high yields while minimizing the production of undesirable impurities and/or partially brominated materials.

In accordance with this invention, there is provided a process for the manufacture of a polybrominated indane product. The process comprises the steps of:

(a) forming an intermediate by reacting an indane compound with bromine, under reaction conditions so as to dissolve and partially ar-brominate the indane compound to contain an average of at least about two at-bromine atoms per molecule, and (b) catalytically ar-brominating the intermediate to obtain a polybrominated indane product, the catalytic ar-bromination occurring in the presence of an aluminum or iron-containing bromination catalyst or other bromination catalyst having a catalytic activity substantially equivalent thereto and in a mole ratio of bromine to said intermediate of at least five.

As used herein, ar-bromination, ar-bromine and the like all relate to bromine substitution on an aromatic carbon. This is to distinguish from bromine addition to an alkyl carbon.

The term "indane compound" as used herein means indane as well as aromatic and hydroaromatic compounds which include the indane nucleus, i.e., a fused 5 and 6-membered ring structure. Non-limiting examples of such indane derivatives include; 3-(diphenylmethylene) indene, 1-phenyl-3-benzylidene indene, spiro(cyclopentane-1,1'-indene), 1,1'spirobiindene, fluorene, and the like. Such compounds can be represented by one or another of the following general formulas:

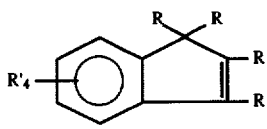

-continued

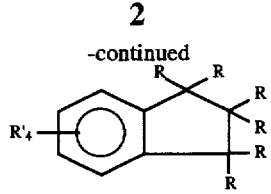

where each R is individually hydrogen, $C_1$ to $C_{20}$ alkyl or substituted alkyl, $C_1$ to $C_{20}$ alkenyl or substituted alkenyl, $C_6$ to $C_{30}$ aryl or substituted aryl, $C_3$ to $C_{20}$ cycloalkyl or substituted cycloalkyl, $C_1$ to $C_{30}$ alkylaryl or substituted alkylaryl and the like, and where each R' is as defined for R and also including halogen and where any two R and/or R', groups can be joined to form a $C_5$ to $C_{13}$ ring or substituted ring structure.

The preferred indanes which are to be brominated by the process of the invention for use as flame retardants in plastics are phenyl indanes represented by the general formula:

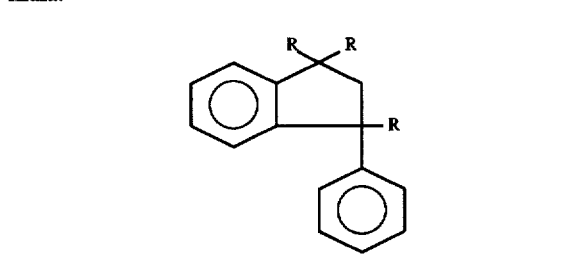

where each R is individually hydrogen or $C_1$ to $C_{10}$ alkyl. Non-limiting examples of such compounds include 1-methyl-3-phenyl indane, 1,3,3-trimethyl-1-phenyl indane, and the like.

The phenyl rings can also be substituted with a lower alkyl and/or halogen, e.g., compounds such as 6-chloro-1, 3,3-trimethyl-1-(4-chlorophenyl) indane, but are preferably unsubstituted. The 1-methyl-3-phenyl indane can be prepared by condensing two molecules of styrene and the 1,3,3-trimethyl-1-phenyl indane can be prepared by the dimerization of alpha-methylstyrene as is known in the art.

It is preferred that the bromine used in the process of this invention be essentially anhydrous, i.e., contain less than 100 ppm water, and contain no more than 10 ppm by weight of organic impurities, e.g., oil, grease, carbonyl containing hydrocarbons, iron, and the like. With such a bromine purity, there is little, if any, impact on the color attributes of the polybrominated indane product. Available, commercial grade bromine may have such purity. If, however, such is not available, the organic impurities and water content of the bromine can be conveniently reduced by mixing together a 3 to 1 volume ratio of bromine and concentrated (94–98 percent) sulfuric acid. A two-phase mix is formed which is stirred for 10–16 hours. After stirring and settling, the sulfuric acid phase, along with the impurities and water, is separated from the bromine phase. To further enhance the purity of the bromine, the recovered bromine phase can be subjected to distillation.

In the first stage of the process of the invention, the indane compound and bromine are preferably reacted by simply mixing one with the other using almost any conventional technique. For example, the mixing can be accomplished by using a mixing nozzle, in-line mixer, annular mixer, impingement mixer and the like. The mixing device can be internal or external to the reactor. It is most convenient to use a impingement mixer at the distal end of a dip feed tube which extends to a location within the reactor and subsurface of the reaction mass. The indane compound can be fed to the mixer as a solid or liquid feed. It is preferred that the indane feed be molten. The indane compound dissolves in the bromine which is necessary for bromination to occur.

The molar ratio of bromine to phenyl indane used to form the desired mixture lies within the range of from about 5:1 to about 30:1, and preferably within the range of from about 7.5:1 to about 25:1. Most preferably, the molar ratio lies within the range of from about 9:1 to about 25:1. Most highly preferred is a ratio within the ratio of about 10:1 to 15:1. Molar ratios in excess of 30:1 may be used; however, such excess ratios will result in more liquid bromine being present after the completion of the bromination process and thus, higher attendant costs for the bromine recovery step.

The indane and bromine are reacted for times and at temperatures such that the indane is only partially ar-brominated in the first step by substitution of bromine for hydrogen on the phenyl rings. The partially brominated indane intermediate needs to contain an average of at least about two gram atoms, and preferably from about two to four gram atoms, of ar-bromine per gram mole of indane reactant. It should be understood that individual molecules of the indane may be aromatically mono-, di-, tri-, and tetra-substituted. The reaction conditions must be mild enough such that cleavage of the 5-membered ring at the benzylic carbon is minimized prior to the partial bromination of the indane compounds. This initial partial bromination is believed to stabilize the indane molecule and minimize the amounts of impurities such as, in the case of phenyl indanes, hexabromobenzene, hexabromonapthalene and brominated biphenyls in the final product. The use of temperatures of from about 0° C. to reflux (60° C.) are preferred for the first stage bromination. Higher temperatures can be used, either by employing superatmospheric pressures or by including a higher boiling inert organic liquid in the reaction mixture. Non-limiting examples of suitable inert, organic liquids include, lower alkyl halides such as methylene bromide, ethylene dichloride, methylene chloride, ethylene dibromide, chloroform, carbon tetrachloride and the like.

It is preferred that the partial bromination step be accomplished without using any catalyst, i.e., the reaction is free of catalytically significant amounts of catalyst. However, it is permissible to lightly catalyze the partial bromination. For example, a weak Lewis acid catalyst such as antimony chlorides, tin chlorides, zinc chloride, bismuth chloride, cadmium chloride, and the like, can be used in an amount of from about 0.001 to 0.1 gram per gram of indane compound. Also, very small amounts, e.g., from about 0.001 to 0.005 gram per gram of indane compound, of a strong Lewis acid catalyst such as $AlCl_3$ or $FeBr_3$ can be used. These catalyst systems are effective to obtain partial ar-bromination of the indane without significant cleaving of the indane molecule.

Total reaction times of from about 5 minutes to two hours are usually sufficient to achieve the partial ar-bromination of the indane compound to form the intermediate product which is then further brominated in the second stage of the process of the invention.

In the second stage of the process of the invention, the partially ar-brominated indane intermediate is further brominated to form a product which is, preferably, predominantly fully ar-brominated, i.e., in the case of a phenyl indane, an octabromo-phenyl indane. Such high bromine content materials are preferred for use as flame retardant additives in plastics. Although the phenyl indanes have up to nine aromatic ring carbon atoms available for substitution, one of the carbon atoms on the phenyl group is sheltered by steric effects due to the folded configuration of the phenyl indane molecule and so usually remains unsubstituted. In order to provide the ar-perbromination needed to obtain an octabrominated product, a strong Lewis Acid bromination catalyst system is used.

Aluminum or iron-containing bromination catalysts are preferred, e.g., $AlCl_3$, $FeBr_3$, and/or $AlBr_3$, although use may be made of aluminum powder, iron powder, $FeCl_3$, $FeBr_3$, $ZrCl_4$ and the like either alone or in combination with the aluminum trihalides. Using an iron-containing catalyst usually provides a colored product. Other strong Lewis acid bromination catalysts may be suitable, provided that they have sufficient catalytic activity to provide for the ar-bromination needed. Catalytic quantities are used. Typically, the catalyst will be present in an amount within the range of from about 0.1 to about 20 weight percent, based on the weight of the indane reactant. The amount used will generally depend on the catalytic activity of the chosen catalyst, the reaction temperature, and the amount of bromine used. A preferred amount is within the range of from about 2 to about 15 weight percent based on the weight of indane. When $AlCl_3$ is the catalyst, for example, from about 3.0 to 5.0 weight percent will be most preferred.

The catalyst can be combined with the intermediate product by mixing the catalyst with the first stage reaction mixture either alone or or in combination with additional bromine in any manner and order so long as suitable control of the resulting reaction and HBr evolution can be maintained. In a preferred embodiment, the first stage reaction mixture is added to an agitated, glass or glass-lined reactor to which has already been charged additional bromine and the bromination catalyst.

The bromination catalyst and bromine can be charged to the reactor in any order or together. The first stage reaction mixture is then added to the reactor in a few minutes time and reacted at temperatures of from about 50° C. to 80° C. or higher. Temperatures above 60° C. require either the addition of higher boiling inert organic liquid or pressurized operation.

The amount of bromine in the reaction mass during the feed of the stage 1 reaction mixture to prepare the preferred products is that amount which is sufficient to yield a stirrable reaction mass and, ultimately, in the case of the phenyl indanes, a predominantly octabromophenyl indane (such a product is defined as a mixture of brominated phenyl indanes having a bromine number of at least about 7.0 and preferably within the range of from about 7.5–8). There are two sources of bromine which will contribute bromine to the reaction mass—the bromine which accompanies the stage 1 reaction mixture and the bromine which is initially present in the reactor with the catalyst. The amount of bromine initially present in the reactor is preferably within the range of from about 25 to about 150% of the stoichiometric amount needed to produce the brominated indane product. Most preferred is an initial bromine amount which is within the range of from about 75% to about 125% of the stoichiometric amount.

The total amount of bromine, that is the sum of the amount of initial bromine in the reactor and the amount of bromine used in forming the stage 1 reaction mixture, will provide a molar ratio of bromine to the indane used which is within the range of from about 14:1 to about 30:1. Preferred for phenyl indanes is a molar ratio of from about 16:1 to about 21:1 and most preferred is a molar ratio of from about 18:1 to about 20:1.

During the feed of the stage 1 reaction mixture, the reaction mass temperature is kept within the range of from about 10° C. to about 80° C., and preferably within the range of from about 20° C. to about 30° C. Since the bromination of the indanes is exothermic, cooling of the reaction mass is needed to maintain the reaction mass temperature chosen. The heat of reaction can be removed from the reaction mass by cooling the reaction vessel or by having the reaction mass under reflux conditions so that heat can be removed by the use of an overhead condenser. When the feed has been completed, the reaction mass is, preferably, kept at reflux.

It is preferred that the pressure in the reaction vessel be that which provides a refluxing condition at the selected reaction mass temperature. With a refluxing condition, control of the reaction mass temperature is facilitated. If temperature control is effected otherwise, i.e., by the use of heating or cooling jackets, then the pressure can be any which is not prohibitive of the obtainment of the various defined parameters of the process. Also, since temperatures above the boiling point of bromine are useful in the process of this invention, super atmospheric pressure, e.g., 15 psig can be used to obtain same.

The second stage bromination reaction is usually completed after from about 0.5 to 3 hours, but longer or shorter times can be used. When the reaction is completed, HBr evolution will cease. Prior to product recovery, it is preferred to first deactivate the catalyst. Deactivation can be accomplished by introducing water to the cooled reaction mass or vise-versa. Water and bromine can then be stripped such as by steam distillation to recover a solid product.

After the bromine has been stripped off, the product is treated with an aqueous base to neutralize any HBr present. The base can be any suitable base, e.g., an aqueous solution of NaOH or $Na_2CO_3$. The product is then washed with water to remove the base and can also be solvent washed, for example with acetone, if necessary, to remove color bodies. The product can be further purified such as by recrystallization using, for example, toluene.

The process of the invention uses a large molar excess of bromine, preferably about 190% or more, which acts as the reaction medium as well as providing the reactant. The process can provide a crude ar-brominated phenyl indane product in almost quantitative yield and final products having a purity of 94–95% ($Br_8$ isomer) which contains only about 1–2% by weight of underbrominated product. In contrast, the prior art bromine in solvent process provides products which contain 10 weight percent or more of underbrominated material.

The invention is further illustrated by, but is not intended to be limited to, the following examples.

EXAMPLE 1

A 250 ml flask was charged with $Br_2$ (30 ml) and then 11.8 g of TMPI(1,3,3-trimethyl-1-phenyl indane) was added in small portions at 23°–25° C., in 30 minutes. The flask was slightly shaken after each addition, and the low amount of HBr evolved was exited to air via a drying tube attached to one neck of the flask. When the addition was complete, a very clear solution of TMPI in bromine formed with no precipitate seen. Another 250 ml round bottomed flask was equipped with a thermometer, a temperature regulator, an addition funnel with a needle valve, a mechanical stirrer and a reflux condenser fitted with a tube leading to a caustic scrubber. The addition funnel on the reactor flask was charged with the partially brominated TMPI/bromine solution, prepared as above. The reactor flask was charged with bromine (30 ml) and then with $FeBr_3$ (1.5 g) and stirred. The TMPI/bromine solution was added to the stirred $Br_2$/$FeBr_3$ solution dropwise, in 10 minutes, at 23°–25° C. A quite vigorous reaction ensued during this addition. The HBr evolved was quenched in the caustic scrubber. The contents were stirred at room temperature for 15 minutes and then heated to reflux (60° C.) for 30 minutes. At the end of 30 minutes the reaction appeared to be over, as no more HBr appeared to be evolved. This reaction mixture was stirred at 60° C. for an additional hour (total at 60° C.=1.5 hours) and then cooled to 25° C. Another 1.5 grams of $FeBr_3$ catalyst were added and the mixture was heated to reflux. Moderate evolution of gas was noted when the temperature reached 40°–60° C. The reaction mixture was heated and stirred at 60° C. for another hour (total at 60° C.=2.5 hours, total catalyst added=3.0 g). The reaction mixture was cooled to room temperature, 150 ml of water were added and $Br_2$/$H_2O$ was steam distilled from the mixture. After a total of 32.0 ml of bromine were distilled off, the heat was cut off and the reaction mixture was allowed to cool to room temperature. The solid product stuck to the flask was scraped off and then NaOH (10 ml, 50% aq. solution) was added. The material turned deep red upon caustic addition. The NaOH/product mixture was stirred for 5 minutes, filtered and washed with water. The color remained. The dried red solid was removed from the filter, ground and washed with water and acetone (3×100 ml). No color improvement was seen. The final octabromo-1,3,3-trimethyl-1-phenyl indane product was a mustard colored solid weighing 37.0 grams, which corresponds to an 85.25% yield. The purity, as determined by G.C. area %, was 98.4% with 1.6% of an unidentified material, (assumed to be hexabromobenzene).

EXAMPLE 2

A 250 ml 3-necked round bottomed flask, equipped with a thermometer, an addition funnel, a magnetic stirrer and a caustic scrubber, was charged with trimethylphenyl indane (TMPI, 11.8 g). Bromine (30 ml) was charged into the addition funnel and added dropwise to the TMPI at about 10 minutes. The reaction temperature rose from 23° to 25° C. during this time. This generated a solution of partially brominated TMPI in bromine. A 500 ml, 4-necked flask equipped with a thermometer, a temperature regulator, addition funnel, a mechanical stirrer and a reflux condenser was charged with bromine (30 ml). After cooling to 8° C. in an ice bath, iron powder (0.2 g) was added and stirred. No adverse reaction was seen and so the ice bath was removed. The addition funnel was charged with the reaction mixture prepared above which was then added to the stirred $Fe$/$Br_2$ solution in about 17 minutes starting at 10° C. The temperature rose to 22° C. and a fast reaction occurred after about 10 minutes. The reaction became slow upon completion of the addition. The mixture was stirred at 23° C. for a few minutes more and then heated to 45° C. A slow reaction was seen when 45° C. was reached but then a sudden exotherm to 60° C. was observed and bromine reflux was seen. The temperature was then maintained at 60° C. for the next two hours. After two hours at 60° C., the reaction mixture was cooled to 45° C., and 250 ml water was added and stirred. Excess bromine was then distilled. At 75°–80° C., the product appeared to be sticking to the sides of the reactor. However, at 90° C. the reaction mass converted to a slurry. After a vapor temperature of 100° C. was reached, the heat was discontinued and the reaction slurry was cooled to 80° C. The product was red in color. Some sodium metabisulfide was added but no color change was seen. The mixture was then cooled to 45° C., NaOH was added (5 ml, 50% aqueous solution) to the slurry, stirred and then filtered. The solid product on the filter was washed with water and allowed to dry overnight in air. The dry product included a few large lumps but was mostly powder and orange in color. The product weighed, 42.2 grams (97.2%) yield.

EXAMPLE 3

A solution of partially brominated TMPI in bromine was prepared by adding Br$_2$(30 ml) to TMPI(11.8 g) in about 9 minutes with the heat evolved raising the temperature from 23° to 28° C. The scrubber gained 8.5 g and the reaction still appeared to be going which indicated at least about 26% of the theoretical amount (32.4 g) of HBr for octabromination had occurred. A reactor set up as in Example 2 was charged with bromine (30 ml), followed by the addition of 0.8 g of anhydrous AlCl$_3$. The partially brominated TMPI/Br$_2$ solution prepared above was added dropwise to the stirred Br$_2$/AlCl$_3$ slurry in 20 minutes, at 23° C. The rate of addition was slow enough to not let the temperature rise above 23° C. The mixture was then stirred for 15 minutes at 23° C. The scrubber gained 19.5 g at this point (total=19.5+8.5 g given off during TMPI/Br$_2$ solution preparation, =28.0 g vs. theory=32.0 g). The reaction was then heated to 45° C. At 30° C. more HBr appeared to be evolving. Within 2 minutes of the temperature reaching 45° C., an exotherm to 48° C. was noticed. The mixture was stirred at 45° C. for 3 hours and 45 minutes, then cooled. Water was added (200 ml) dropwise, in about 5 minutes to decompose the catalyst. Bromine was steam distilled to a vapor temperature of 100° C. (collected 27 ml Br$_2$). The remaining mixture was cooled to 60° C. and 5 ml NaOH (50% aqueous solution) was added with stirring. The filtered product was a mixture of chunks and powder which was hand ground in a pestle, washed with water (35×100 ml) and dried in an oven at 105° C. for thirty minutes. The crude product was yellow and weighed 45.2 grams. After being ground in a blender, the product was placed in an oven at 145° C. After 0.5 hours at 145° C., Br$_2$ vapors were observed to be given off and the product was left at 145° C. overnight. After overnight treatment at 145° C., a dark material weighing 42.6 g was obtained. This material was washed with toluene (6×100 ml). Quite a bit of product dissolved/filtered thorough into the filtrate which was very dark. The washed product was allowed to dry in air to give a light gray solid weighing 27.0 grams (62.2%). G.C. analysis showed 97.7% pure octabromo-1,3,3-trimethyl-1-phenyl indane product, with only 2.2% hexabromobenzene present as an impurity.

EXAMPLE 4

A 250 ml 3-necked round bottomed flask equipped with a reflux condenser, a thermometer with a Therm-o-watch, a caustic scrubber, stirrer, heating mantle and an addition funnel was charged with molten TMPI (28.9 g) which solidified in the flask. Bromine (60 ml) was added to the TMPI dropwise in 10 minutes. After a few drops of bromine had been added, stirring was commenced. During the bromine addition, vigorous HBr evolution initially occurred which slowed as the bromine addition was completed. The temperature of the mixture rose from 24° C. to 35° C. during the addition. The scrubber gained 20.0 grams in weight. The reaction mixture was heated to reflux at 59° C. for one hour with stirring. The total weight gained by the scrubber was 30.8 grams. The reaction slurry/solution was cooled and transferred to an addition funnel which was installed on a 1-liter, 4-necked round bottomed flask. The reaction flask was also equipped with a thermometer, mechanical stirrer, scrubber, reflux condenser and a temperature regulator. The reactor was charged with fresh bromine (60 ml) followed by 1.0 gram of AlCl$_3$ and stirred. The TMPI/Br$_2$ intermediate prepared above was then added dropwise at 23° C. during about 18 minutes. After stirring for an additional two minutes at 23° C., the reaction mixture was heated to reflux. The scrubber gained 45.2 grams. The reaction mixture was stirred at reflux (60° C.) for an hour and then cooled. The scrubber gain during the addition and reflux was 54.5 grams. The total scrubber gain during the TMPI/Br$_2$ slurry/solution preparation and catalyzed bromination was 85.3 grams (theory 64.8 grams) indicating that some bromine was also absorbed along with the HBr. The reaction mixture was cooled and 250 ml of water were added. The mixture was then heated to steam distill the excess bromine to a vapor temperature of 100° C. A total of 46 ml of bromine was collected. This gave a crude product in the form of a light orange powder slurry in water with no chunks. A sample of product was dissolved in methylene bromide and analyzed by G.C. The analysis indicated that the crude product was 93.8% octabromo-1,3,3-trimethyl-1-phenyl indane, 4.4% hexabromobenzene and only 1.8% of underbrominated material, the presence of which in excessive amounts is believed to cause lumping. This product was not purified further but several purification procedures can be used to enhance the purity of the crude product. For example, the crude product can be further purified by heating and grinding in either order or simultaneously to remove any trapped bromine. The product can also be stirred in water, added to methylene bromide, refluxed and collected on a filter. Alternatively, sufficient solvent can be added to completely dissolve the product at elevated temperature such that the purified product crystallizes out on cooling.

COMPARISON

A reactor was charged with 1600 grams of bromine, 1.5 grams of anhydrous AlCl$_3$ was added and the mixture was stirred for about 15 minutes. An addition funnel was charged with 8.5 grams of TMPI which was then melted with a heat gun and added to the bromine/catalyst mixture in about 5–6 minutes. A vigorous reaction, as evidenced with the evolution of HBr gas, occurred throughout the addition. The mixture was stirred and heated to reflux (60° C.) and maintained at reflux for 5.5 hours. The mixture was then cooled, 100 ml of water was added and the excess bromine was steam distilled. A sticky ball formed after some of the bromine had been distilled off. This created a severe agitation problem. A total of 19 ml of bromine was collected. Distillation was stopped a bit prematurely due to the agitation problem. However, after cooling and standing overnight no free bromine was left. Residual HBr was neutralized by adding 8 ml of 50% aqueous NaOH with stirring. The solid was broken into pieces, and ground to a powder. Oven drying at 110° C. for 3 hours gave 45.9 grams (0.05 mole, 121.2% yield) of a reddish orange product. The over-theory yield suggested there was over-bromination by perhaps cleavage of the molecule. In fact, G.C. analysis in dibromomethane, showed 6 major components, of which, only 13% appeared to be the desired product. There was about 48% hexabromobenzene, formed by cleavage. Solid probe mass spectral analysis showed the presence of, besides the hexabromobenzene, hexabromonaphthalene, brominated biphenyls as well as the desired octabromo-1, 3,3-trimethyl-1-phenyl indane as major products.

The above comparison demonstrates the yield and impurity problems which can occur when the phenyl indane is not pre-brominated.

What is claimed is:

1. A process for the manufacture of a polybrominated indane product, said process comprising the steps of:
    (a) forming an intermediate by reacting an indane compound with bromine, under reaction conditions so as to dissolve and partially ar-brominate the indane compound to contain an average of at least about two ar-bromine atoms per molecule, the reaction occurring in the presence of from about 0.001 to about 0.1 gram per gram of indane compound of a weak Lewis acid catalyst selected from the group consisting of antimony chlorides, tin chloride, zinc chloride, bismuth chloride, and cadmium chloride or of from about 0.001 to about 0.005 gram per gram of indane compound of a strong Lewis acid catalyst selected from the group consisting of iron containing bromination catalyst, an aluminum containing bromination catalyst, and zirconium tetrachloride bromination catalyst; and (b) catalytically ar-brominating the intermediate to obtain a polybrominated indane product, the catalytic ar-bromination occurring in the presence of aluminum containing bromination catalyst or iron containing bromination catalyst or zirconium tetrachloride bromination catalyst and in a mole ratio of bromine to said intermediate of at least 5.

2. A process for the manufacture of a polybrominated phenyl indane product, said process comprising the steps of:

(a) forming an intermediate by reacting a phenyl indane compound with bromine, under reaction conditions so as to partially ar-brominate the phenyl indane to contain an average of at least about two to about four ar-bromine atoms per molecule, the reaction occurring without the presence of a catalytic amount of a bromination catalyst; and (b) catalytically ar-brominating the intermediate to obtain a polybrominated phenyl indane product, containing an average of at least about seven ar-bromine atoms per molecule, the catalytic bromination occurring in the presence of aluminum containing bromination catalyst or iron containing bromination catalyst or zirconium tetrachloride bromination catalyst and in a mole ratio of bromine to said intermediate of at least 5.

3. The process according to claim 2 wherein additional bromine is added in step (b).

4. The process according to claim 3 wherein the molar ratio of total bromine present in the process to phenyl indane compound is at least about 14.

5. The process according to claim 4 wherein said molar ratio is from about 14 to 30.

6. The process according to claim 2 wherein said bromination catalyst is a Lewis acid.

7. The process according to claim 6 wherein said catalyst is selected from the group consisting of halides of iron, aluminum, and zirconium.

8. The process according to claim 2 wherein said phenyl indane is 1,3,3-trimethyl-1-phenyl indane and said polybrominated phenyl indane product is predominantly octabromo-1,3,3-trimethyl-1-phenyl indane.

9. The process according to claim 2 wherein said phenyl indane is 1-methyl-3-phenyl indane and said product is predominately octabromo-1-methyl-3-phenyl indane.

10. The process according to claim 2 wherein bromination catalyst system is present in step (a).

11. The process according to claim 2 wherein in step (b) the reaction mixture from step (a) is added to a mixture of bromine and catalyst and the resulting reaction mixture is refluxed so as to produce a polybrominated phenyl indane product which contains an average of at least about 7.5 bromine atoms per molecule of phenyl indane.

* * * * *